United States Patent
Harris et al.

(10) Patent No.: US 10,934,597 B2
(45) Date of Patent: Mar. 2, 2021

(54) COMPOSITIONS AND METHODS FOR DETECTION OF TRICHOMONAS VAGINALIS

(71) Applicant: Roche Molecular Systems, Inc., Pleasanton, CA (US)

(72) Inventors: Jody Harris, Lafayette, CA (US); Shi-Da Y. Lu, Oakland, CA (US); Kalyani Mangipudi, Pleasanton, CA (US); Jingtao Sun, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/601,495

(22) Filed: May 22, 2017

(65) Prior Publication Data

US 2017/0342508 A1 Nov. 30, 2017

Related U.S. Application Data

(60) Provisional application No. 62/342,600, filed on May 27, 2016.

(51) Int. Cl.
| | |
|---|---|
| *C07H 21/04* | (2006.01) |
| *C12Q 1/68* | (2018.01) |
| *C12Q 1/6893* | (2018.01) |
| *C12Q 1/689* | (2018.01) |

(52) U.S. Cl.
CPC .......... *C12Q 1/6893* (2013.01); *C12Q 1/689* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2012/0141992 A1 | 6/2012 | Singhal et al. |
| 2012/0142003 A1* | 6/2012 | Barfield ............... C12Q 1/6893 435/6.12 |

FOREIGN PATENT DOCUMENTS

WO 2012075317 A2 6/2012

OTHER PUBLICATIONS

Ma et al. (PLOS one, vol. 5, pp. e15660, Dec. 10, 2010) (Year: 2010).*
Felleisen et al. (Parasitology, vol. 115, pp. 111-119, 1997) (Year: 1997).*
GenBank Accession No. U86613, Jan. 26, 2001.
GenBank Accession No. NW_001533462, Jan. 30, 2009.
GenBank Accession No. NW_001581675, Jan. 30, 2009.
GenBank Accession No. XM_001320341, Nov. 2, 2008.
GenBank Accession No. XM_001581132.
Carlton, JM, et al., "Draft genome sequence of the sexually transmitted pathogen Trichomonas vaginalis", Science Jan. 12, 2007;315(5809)207-12.
Dwivedi, S.P., et al., 18S ribosomal DNA based PCR diagnostic assay for Trichomonas vaginalis infection in symptomatic and asymptomatic women in India, Asian Pacific Journal of Tropical Disease, Apr. 2012, pp. 133-138, vol. 2, No. 2.
Hobbs, M.M., et al., Modern diagnosis of Trichomonas vaginalis infection, Sexually Transmitted Infections, Apr. 2013, pp. 434-438, vol. 89, No. 6.
International Search Report and Written Opinion dated Oct. 2, 2017 in corresponding PCT/EP2017/062509 filed on May 24, 2017, pp. 1-21.
Mayta, H., et al, 18S Ribosomal DNA-Based PCR for Diagnosis of Trichomonas vaginalis, Journal of Clinical Microbiology, Jul. 2000, pp. 2683-2687, vol. 38, No. 7.
Partial International Search Report dated Aug. 8, 2017 in Application No. PCT/EP2017/062509, 17 pages.
Torres-Machorro, A.L., et al., Comparative analyses among the Trichomonas vaginalis, Trichomonas tenax, and Tritrichomonas foetus 5S ribosomal RNA genes, Current Genetics, Apr. 2009, pp. 199-210, vol. 55, No. 2.
Crucitti, T. el al., Trichomonas vaginalis is Highly Prevalent in Adolescent Girls, Pregnant Women, and Commercial Sex Workers in Ndola, Zambia, Sexually Transmitted Diseases, vol. 37(4), 223-227, 2010.
Brosh-Nissimov, T. el al., A false-positive Trichomonas vaginalis result due to Trichomonas tenax presence in clinical specimens may reveal a possible T. tenax urogenital infection, Clinical Microbiology and Infection, vol. 25, 123-124, 2019.

* cited by examiner

*Primary Examiner* — Jeanine A Goldberg
(74) *Attorney, Agent, or Firm* — David J. Chang

(57) ABSTRACT

Methods for the rapid detection of the presence or absence of *Trichomonas vaginalis* (TV) in a biological or non-biological sample are described. The methods can include performing an amplifying step, a hybridizing step, and a detecting step. Furthermore, primers, probes targeting the target TV gene, along with kits are provided that are designed for the detection of TV.

5 Claims, 4 Drawing Sheets

Specification includes a Sequence Listing.

US 10,934,597 B2

COMPOSITIONS AND METHODS FOR DETECTION OF TRICHOMONAS VAGINALIS

CROSS REFERENCE TO RELATED APPLICATIONS

This application claims the benefit of priority of U.S. Provisional Patent Application Ser. No. 62/342,600, filed May 27, 2016, which is incorporated herein by reference in its entirety.

REFERENCE TO SEQUENCE LISTING

This application contains a Sequence Listing submitted as an electronic text file named "33593_US1_Sequence_Listing.txt", having a size in bytes of 30 kb, and created on Apr. 17, 2017. The information contained in this electronic file is hereby incorporated by reference in its entirety pursuant to 37 CFR § 1.52(e)(5).

FIELD OF THE INVENTION

The present disclosure relates to the field of molecular diagnostics, and more particularly to detection of *Trichomonas vaginalis*.

BACKGROUND OF THE INVENTION

*Trichomonas vaginalis* (TV) is a flagellated protozoan parasite that causes trichomoniasis, the most prevalent non-viral sexually transmitted infection in the United States, affecting an estimated 3.7 million persons nationwide. The prevalence differs among black and non-Hispanic white women with 13% compared to 1.8% affected, respectively. *T. vaginalis* infection has been reported to affect >11% of women aged 40 years and prevalence rates have been reported as high as 26% in symptomatic women and 6.5% in asymptomatic women tested at STD clinics. *T. vaginalis* is also known to cause urethritis in men who have sex with women (MSW). Most infections go unnoticed, with 70% of men and 85% women experiencing only minor symptoms and if untreated may last for months or years. Asymptomatic spread of infection does occur and remains a problem. Infections in women include vaginitis, cervicitis and urethritis. Symptomatic women usually complain of vaginal discharge, vulvovaginal soreness, and/or irritation. Dysuria is also common. Complications can include premature labor, low-birth-weight offspring, premature rupture of membranes, and post-abortion or post-hysterectomy infection. An association with pelvic inflammatory disease (PID), tubal infertility, and cervical cancer with previous episodes of trichomoniasis has been reported. Symptoms in men may include urethritis, epididymitis, or prostatitis.

*T. vaginalis* infection is associated with two- to three-fold increased risk for HIV acquisition, preterm birth, and other adverse pregnancy outcomes among pregnant women. Among women with HIV infection, *T. vaginalis* infection is associated with increased risk for pelvic inflammatory disease (PID). Routine screening of asymptomatic women with HIV infection for *T. vaginalis* is recommended because of the adverse events associated with asymptomatic trichomoniasis and HIV infection. Diagnostic testing for *T. vaginalis* should be performed in women seeking care for vaginal discharge. Screening might be considered for persons receiving care in high-prevalence settings (e.g. STD clinics and correctional facilities) and for asymptomatic persons at high risk for infection (e.g. persons with multiple sex partners, illicit drug use, or a history of STD).

Before molecular methods became available, culture was considered the gold standard method for diagnosing *T. vaginalis* infection but the sensitivity of culture has been estimated to range from 38% to 82% when compared to molecular methods. For culture in women, vaginal secretions are the preferred over urine since urine culture has been shown to be less sensitive. In men, culture specimens require a urethral swab, urine sediment, and/or semen. Culture of multiple specimens from men used to inoculate a single culture may improve sensitivity. The microscopic examination of wet preparations of genital secretions is probably the most common method for *T. vaginalis* diagnosis because of convenience and relatively low cost but is only 35% to 80% sensitive compared with culture. Moreover, the sensitivity of the wet-mount method is highly dependent on the experience of the microscopist as well as the time of specimen transport to the laboratory where sensitivity declines by up to 20% within 1 hour after collection. Thus there is a need in the art for a quick and reliable method to specifically detect TV in a sensitive manner.

SUMMARY OF THE INVENTION

Certain embodiments in the present disclosure relate to methods for the rapid detection of the presence or absence of TV in a biological or non-biological sample, for example, multiplex detection of TV by real-time polymerase chain reaction in a single test tube. Embodiments include methods of detection of TV comprising performing at least one cycling step, which may include an amplifying step and a hybridizing step. Furthermore, embodiments include primers, probes, and kits that are designed for the detection of TV in a single tube. The detection methods are designed to target specific genes in the *T. vaginalis* genome with a potential to discriminate against the nearest neighbors *Trichomonas tenax* and A method for detecting TV in a sample is provided, including performing an amplifying step including contacting the sample with a set of primers designed to target a specific TV gene to produce an amplification product if TV is present in the sample; performing a hybridizing step including contacting the amplification product with one or more detectable probes to the target TV gene; and detecting the presence or absence of the amplified product, wherein the presence of the amplified product is indicative of the presence of TV in the sample and wherein the absence of the amplified product is indicative of the absence of TV in the sample; wherein the target TV gene is selected from the group consisting of the 5.8 s ribosomal RNA (5.8s) gene, the 18s (or 16s-like) ribosomal RNA (18s) gene, the DNA mismatch repair homolog, post-meiotic segregation increased-1 (PMS1) gene, the MutL homolog 1a (Mlh1a) gene, and the coronin (CRN) gene. FIG. 1 shows the location of the 5.8s gene, the inter-transcribed sequence 2 (ITS2) and neighboring genes in the TV genome.

In one aspect a method of detecting *Trichomonas vaginalis* (TV) in a sample is provided, the method comprising performing an amplifying step comprising contacting the sample with a set of target TV gene primers to produce an amplification product if a target TV gene nucleic acid is present in the sample; performing a hybridizing step comprising contacting the amplification product with one or more detectable target TV gene probes; and detecting the presence or absence of the amplification product, wherein the presence of the amplification product is indicative of the presence of TV in the sample and wherein the absence of the amplification product is indicative of the absence of TV in the sample; wherein the set of target TV gene primers comprise a first primer comprising or consisting of a first oligonucleotide sequence selected from the group consisting of SEQ ID NOs: 1-9, 19-28, 45-48, 55-64, and 80-89 or a complement thereof, and a second primer comprising or consisting of a second oligonucleotide sequence selected from the group consisting of SEQ ID NOs: 10-13, 29-38, 49-52, 65-74, and 90-99, or a complement thereof; and wherein the one or more detectable target TV gene probes comprises or consists of a third oligonucleotide sequence selected from the group consisting of SEQ ID NOs: 14-18, 39-44, 53-54, 75-79, and 100-105, or the complement thereof.

In one embodiment, the primer set for amplification of the 5.8s gene target includes a first primer comprising or consisting of a first oligonucleotide sequence selected from the group consisting of SEQ ID NOs: 1, 2, 3, 4, 5, 6, 7, 8, and 9, or a complement thereof, and a second primer comprising or consisting of a second oligonucleotide sequence selected from the group consisting of SEQ ID NOs: 10, 11, 12, and 13, or a complement thereof, and the detectable probe for detection of the 5.8s gene amplification product includes or consists of the nucleic acid sequences of SEQ ID NOs: 14, 15, 16, 17, and 18, or a complement thereof. In certain embodiments, the primer set for amplification of the 5.8s gene target includes a first primer comprising or consisting of a first oligonucleotide sequence selected from the group consisting of SEQ ID NOs: 3, 6, 7, and 9, or a complement thereof, and a second primer comprising or consisting of a second oligonucleotide sequence selected from the group consisting of SEQ ID NO: 12, or a complement thereof, and the detectable probe for detection of the 5.8s gene amplification product includes or consists of the nucleic acid sequences of SEQ ID NOs: 16, 17, and 18, or a complement thereof.

In another embodiment, the primer set for amplification of the 18s gene target includes a first primer comprising or consisting of a first oligonucleotide sequence selected from the group consisting of SEQ ID NOs: 19, 20, 21, 22, 23, 24, 25, 26, 27, and 28, or a complement thereof, and a second primer comprising or consisting of a second oligonucleotide sequence selected from the group consisting of SEQ ID NOs: 29, 30, 31, 32, 33, 34, 35, 36, 37, and 38, or a complement thereof, and the detectable probe for detection of the 18s gene amplification product includes or consists of the nucleic acid sequences of SEQ ID NOs: 39, 40, 41, 42, 43, and 44, or a complement thereof. In certain embodiments, the primer set for amplification of the 18s gene target includes a first primer comprising or consisting of a first oligonucleotide sequence selected from the group consisting of SEQ ID NOs: 21 and 22, or a complement thereof, and a second primer comprising or consisting of a second oligonucleotide sequence selected from the group consisting of SEQ ID NOs: 31 and 32, or a complement thereof, and the detectable probe for detection of the 18s gene amplification product includes and consists of the nucleic acid sequences of SEQ ID NO: 40, or a complement thereof.

In another embodiment, the primer set for amplification of the PMS1 gene target includes a first primer comprising or consisting of a first oligonucleotide sequence selected from the group consisting of SEQ ID NOs: 45, 46, 47 and 48, or a complement thereof, and a second primer comprising or consisting of a second oligonucleotide sequence selected from the group consisting of SEQ ID NOs: 49. 50, 51 and 52, or a complement thereof, and the detectable probe for detection of the PMS1 gene amplification product includes or consists of the nucleic acid sequences of SEQ ID NOs: 53 and 54, or a complement thereof.

In another embodiment, the primer set for amplification of the Mlh1a gene target includes a first primer comprising or consisting of a first oligonucleotide sequence selected from the group consisting of SEQ ID NOs: 55, 56, 57, 58, 59, 60, 61, 62, 63 and 64, or a complement thereof, and a second primer comprising or consisting of a second oligonucleotide sequence selected from the group consisting of SEQ ID NOs: 65, 66, 67, 68, 69, 70, 71, 72, 73, and 74, or a complement thereof, and the detectable probe for detection of the Mlh1a gene amplification product includes or consists of the nucleic acid sequences of SEQ ID NOs: 75, 76, 77, 78, and 79, or a complement thereof. In certain embodiments, the primer set for amplification of the Mlh1a gene target includes a first primer comprising or consisting of a first oligonucleotide sequence selected from the group consisting of SEQ ID NOs: 57, 58, 63 and 64, or a complement thereof, and a second primer comprising or consisting of a second oligonucleotide sequence selected from the group consisting of SEQ ID NOs: 67, 68, 73, and 74, or a complement thereof, and the detectable probe for detection of the Mlh1a gene amplification product includes or consists of the nucleic acid sequences of SEQ ID NOs: 76 and 79, or a complement thereof.

In another embodiment, the primer set for amplification of the CRN gene target includes a first primer comprising or consisting of a first oligonucleotide sequence selected from the group consisting of SEQ ID NOs: 80, 81, 82, 83, 84, 85, 86, 87, 88 and 89, or a complement thereof, and a second primer comprising or consisting of a second oligonucleotide sequence selected from the group consisting of SEQ ID NOs: 90, 91, 92, 93, 94, 95, 96, 97, 98, and 99, or a complement thereof, and the detectable probe for detection of the CRN gene amplification product includes or consists of the nucleic acid sequences of SEQ ID NOs: 100, 101, 102, 103, 104, and 105, or a complement thereof. In certain embodiments, the primer set for amplification of the CRN gene target include a first primer comprising or consisting of a first oligonucleotide sequence selected from the group consisting of SEQ ID NOs: 80, 81, 82, and 83, or a complement thereof, and a second primer comprising or consisting of a second oligonucleotide sequence selected from the group consisting of SEQ ID NOs: 90, 91, 92, and 93, or a complement thereof, and the detectable probe for detection of the CRN gene amplification product includes or consists of the nucleic acid sequences of SEQ ID NOs: 100 and 101, or a complement thereof.

In some embodiments the hybridizing step comprises contacting the amplification product with the detectable target TV gene probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the probe, wherein the presence or absence of fluorescence is indicative of the presence or absence of TV in the sample. In some embodiments the amplifying and the hybridizing steps are repeated. Herein, the number of repetitions depends, e.g., on the nature of the sample. If the sample is a complex mixture of nucleic acids, more amplifying and hybridizing steps will be required to amplify the target sequence sufficient for detection. In some embodiments, the amplifying and the hybridizing steps are repeated at least about 20 times, but may be repeated as many as at least 25, 30, 40, 50, 60, or even 100 times. Further, detecting the presence or absence of the amplification product may be performed during or after each amplifying and hybridizing step, during or after every other amplifying and hybridizing step, during or after particular amplifying and hybridizing steps or during or after particular amplifying and hybridizing steps, in which—if present—sufficient amplification product for detection is expected. In some embodiments, the amplifying step employs a polymerase enzyme having 5' to 3' nuclease activity. In some embodiments, the donor fluorescent moiety and the corresponding acceptor moiety are within no more than 8-20 nucleotides of each other on the probe. In some embodiments, the acceptor moiety is a quencher. In some embodiments the oligonucleotides comprise or consist of a sequence of nucleotides selected from SEQ ID NOs: 1-105, or a complement thereof have 100 or fewer nucleotides, 50 or fewer nucleotides, 40 or fewer nucleotides or 30 or fewer nucleotides. In some embodiments, the first and second target TV gene primers and detectable target TV gene probe have 40 or fewer nucleotides (e.g. 35 or fewer nucleotides, 30 or fewer nucleotides, etc.).

In another embodiment, the present disclosure provides an oligonucleotide that includes a nucleic acid having at least 70% sequence identity (e.g., at least 75%, 80%, 85%, 90% or 95%, etc.) to one of SEQ ID NOs: 1-105, or a complement thereof, which oligonucleotide has 100 or fewer nucleotides. Generally, these oligonucleotides may be primer nucleic acids, probe nucleic acids, or the like in these embodiments. In some embodiments, the oligonucleotides comprise at least one modified nucleotide, e.g., to alter nucleic acid hybridization stability relative to unmodified nucleotides. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. In some embodiments, at least one of the first and second target TV gene primers and detectable target TV gene probe comprises at least one modified nucleotide.

In some embodiments, amplification (the amplifying step) can employ a polymerase enzyme having 5' to 3' nuclease activity. Thus, the donor fluorescent moiety and the acceptor moiety, e.g., a quencher, may be within no more than 5 to 20 nucleotides (e.g., 8 or 10) of each other along the length of the probe. In another aspect, the detectable probe includes a nucleic acid sequence that permits secondary structure formation. Such secondary structure formation generally results in spatial proximity between the first and second fluorescent moiety. According to this method, the second fluorescent moiety on the probe can be a quencher.

The present disclosure provides for methods of detecting the presence or absence of TV in a biological sample from an individual. Such methods generally include performing at least one cycling step, which includes an amplifying step and a dye-binding step. Typically, the amplifying step includes contacting the sample with a plurality of pairs of primers designed to target a specific TV gene to produce one or more target TV gene amplification products if the target TV gene nucleic acid molecule is present in the sample, and the dye-binding step includes contacting the target TV gene amplification product with a double-stranded DNA binding dye. Such methods also include detecting the presence or absence of binding of the double-stranded DNA binding dye into the amplification product, wherein the presence of binding is indicative of the presence of TV in the sample, and wherein the absence of binding is indicative of the absence of TV in the sample. A representative double-stranded DNA binding dye is ethidium bromide. In addition, such methods also can include determining the melting temperature between the target TV gene amplification product and the double-stranded DNA binding dye, wherein the melting temperature confirms the presence or absence of TV. The target TV gene may include but is not limited to the 5.8s gene, the 18s gene, the PMS1 gene, the Mlh1a gene, and the CRN gene.

In another aspect, the methods of detecting TV in a biological sample from an individual is conducted together with methods to detect *Mycoplasma genitalium* (MG) from the same biological sample due to the asymptomatic nature of individuals infected with TV and/or MG. Primers, probes and kits used for detecting MG are described in U.S. Provisional Patent Application No. 62/342,519, titled "Compositions and methods for detection of *Mycoplasma genitalium*", which is incorporated herein by reference in its entirety. In one embodiment, the methods of detecting TV and MG in the biological sample are performed in the same reaction mixture as a multiplex assay.

In yet another aspect, a kit for detecting one or more nucleic acids of TV is provided. The kit can include one or more sets of primers specific for amplification of the target TV gene; and one or more detectable probes specific for detection of the target TV gene amplification products. The target TV gene may include but is not limited to the 5.8s gene, the 18s gene, the PMS1 gene, the Mlh1a gene, and the CRN gene.

In particular, the oligonucleotide primers and probes disclosed above in connection with the method according to the invention are suitable to being included in a kit according to the invention. Herein, a kit for detecting a nucleic acid of *Trichomonas vaginalis* (TV) is provided comprising a first primer comprising a first oligonucleotide sequence selected from the group consisting of SEQ ID NOs: 1-9, 19-28, 45-48, 55-64, and 80-89, or a complement thereof; a second primer comprising a second oligonucleotide sequence selected from the group consisting of SEQ ID NOs: 10-13, 29-38, 49-52, 65-74, and 90-99, or a complement thereof; and a fluorescently detectably labeled probe comprising a third oligonucleotide sequence selected from the group consisting of SEQ ID NOs: 14-18, 39-44, 53-54, 75-79, and 100-105, or a complement thereof, the detectably labeled probe configured to hybridize to an amplicon generated by the first primer and the second primer. In one aspect, the kit can include probes already labeled with donor and corresponding acceptor moiety, e.g., another fluorescent moiety or a dark quencher, or can include fluorophoric moieties for labeling the probes. The kit can also include at least one of nucleoside triphosphates, nucleic acid polymerase, and buffers necessary for the function of the nucleic acid polymerase. The kit can also include a package insert and instructions for using the primers, probes, and fluorophoric moieties to detect the presence or absence of TV in a sample. In some embodiments, the third detectably labeled oligonucleotide sequence comprises a donor fluorescent moiety and a corresponding acceptor moiety. In some embodiments, the acceptor moiety is a quencher. In some embodiments, at least one of the first, second, and third oligonucleotides comprises at least one modified nucleotide. In some embodiments, the first, second, and third oligonucleotides have 40 or fewer nucleotides.

In another aspect, compositions are provided comprising a set of oligonucleotide primers for amplifying a target TV gene as disclosed above. In some embodiments, the set of target TV gene primers comprises a first primer comprising or consisting of a first oligonucleotide sequence selected from the group consisting of SEQ ID NOs: 1-9, 19-28, 45-48, 55-64, and 80-89 or a complement thereof, and a second primer comprising or consisting of a second oligonucleotide sequence selected from the group consisting of SEQ ID NOs: 10-13, 29-38, 49-52, 65-74, and 90-99, or a complement thereof. In certain embodiments the composition further comprises one or more detectable target TV gene probes comprises or consists of a third oligonucleotide sequence selected from the group consisting of SEQ ID NOs: 14-18, 39-44, 53-54, 75-79, and 100-105, or the complement thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
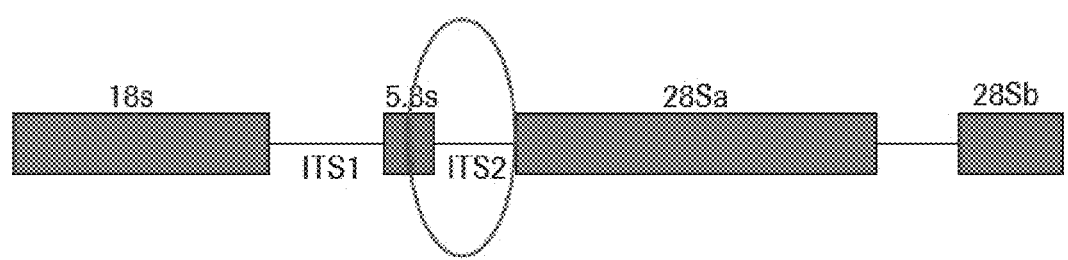
FIG. 1 shows the location of the 5.8s ribosomal RNA gene, the inter-transcribed sequence 2 (ITS2) and neighboring ribosomal genes in the *T. vaginalis* genome.

Diagnosis of TV infection by nucleic acid amplification provides a method for rapidly and accurately detecting the protozoan infection. A real-time assay for detecting TV in a sample is described herein. Primers and probes for detecting TV are provided, as are articles of manufacture or kits containing such primers and probes. The increased sensitivity of real-time PCR for detection of TV compared to other methods, as well as the improved features of real-time PCR including sample containment and real-time detection of the amplified product, make feasible the implementation of this technology for routine diagnosis of TV infections in the clinical laboratory.

The present disclosure includes oligonucleotide primers and fluorescent labeled hydrolysis probes that hybridize to a specific gene locus of the TV genome in order to specifically identify TV using TaqMan® amplification and detection technology. Target selection for TV required a comprehensive search of the public sequence database, as well as literature search for TV targets with a potential to discriminate against the nearest neighbors, *Trichomonas tenax* and *Pentatrichomonas hominis*. Multiple targets from the public sequence database were analyzed in the target selection process but many showed cross reactivity with *T. tenax* and *P. hominis*. Furthermore, sequences in the public database are complicated by "bulk" sequence data from multicopy targets.

As a result of the analysis, possible target TV genes include the 5.8s ribosomal RNA gene (GenBank accession number U86613), the 18s ribosomal RNA gene (GenBank accession number NW001533462), the DNA mismatch repair homolog, post-meiotic segregation increased-1 (PMS1) gene (GenBank accession number NW001581675), the MutL homolog 1a (Mlh1a) gene (GenBank accession number XM001320341) and the coronin (CRN) gene (GenBank accession number XM001581132). In certain aspects, the target TV gene is the 5.8s ribosomal RNA gene as this gene is present in over 200 copies per genome and will hence benefit sensitivity of the assay. Further, the 5.8s ribosomal RNA gene is present in metronidazole resistant and metronidazole sensitive TV and hence allows for the combined detection of both TV types.

The disclosed methods may include performing at least one cycling step that includes amplifying one or more portions of the nucleic acid molecule gene target from a sample using one or more pairs of primers. "Primer(s)" as used herein refer to oligonucleotide primers that specifically anneal to the target gene in TV, and initiate DNA synthesis therefrom under appropriate conditions producing the respective amplification products. Each of the discussed primers anneals to a target within or adjacent to the respective target nucleic acid molecule such that at least a portion of each amplification product contains nucleic acid sequence corresponding to the target. The one or more amplification products are produced provided that one or more of the target TV gene nucleic acid is present in the sample, thus the presence of the one or more of target TV gene amplification products is indicative of the presence of TV in the sample. The amplification product should contain the nucleic acid sequences that are complementary to one or more detectable probes for target TV gene. "Probe(s)" as used herein refer to oligonucleotide probes that specifically anneal to nucleic acid sequence encoding the target TV gene. Each cycling step includes an amplification step, a hybridization step, and a detection step, in which the sample is contacted with the one or more detectable probes for detection of the presence or absence of TV in the sample.

As used herein, the term "amplifying" refers to the process of synthesizing nucleic acid molecules that are complementary to one or both strands of a template nucleic acid molecule. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

Detection of TV

The present disclosure provides methods to detect TV by amplifying, for example, a portion of the target TV gene nucleic acid sequence. Nucleic acid sequences of the 5.8s gene, the 18s gene, the PMS1 gene, the Mlh1a gene and the CRN gene are publicly available (e.g., GenBank). Specifically, primers and probes to amplify and detect specific TV nucleic acid molecule targets are provided by the embodiments in the present disclosure.

For detection of TV, primers and probes to amplify the target TV gene are provided. Nucleic acids other than those exemplified herein can also be used to detect TV in a sample. For example, functional variants can be evaluated for specificity and/or sensitivity by those of skill in the art using routine methods. Representative functional variants can include, e.g., one or more deletions, insertions, and/or substitutions in the target TV gene nucleic acids disclosed herein.

More specifically, embodiments of the oligonucleotides each include a nucleic acid with a sequence selected from SEQ ID NOs: 1-105, a substantially identical variant thereof in which the variant has at least, e.g., 80%, 90%, or 95% sequence identity to one of SEQ ID NOs: 1-105, or a complement of SEQ ID NOs: 1-105 and the variant.

TABLE I

5.8s Forward Primers
Forward Primers

| Oligo Name | SEQ ID NO: | Sequence | Modifications |
|---|---|---|---|
| KMTV5.8s110FBBC | 1 | CCAAGTCTCTAAGCAATGGATGT<t_BB_dC> | t-butylbenzyldC |
| KMTV5.8s117FBBC | 2 | AAGCAATGGATGTCTTGGCT<t_BB_dC> | t-butylbenzyldC |
| KMTV5.8s169FBBC | 3 | TGTTAAGTAACCGGAGTTGCAAA<t_BB_dC> | t-butylbenzyldC |
| KMTV170FBBC | 4 | TTAAGTAACCGGAGTTGCAAA<t_BB_dC> | t-butylbenzyldC |
| KMTV195FBBC | 5 | CAAATTGCGCTAAACTCGATCT<t_BB_dC> | t-butylbenzyldC |
| KMTV203FBBA | 6 | CTAAACTCGATCTCGGTCG<t_BB_dA> | t-butylbenzyldA |
| KMTV201FBBC | 7 | CGCTAAACTCGATCTCGGT<t_BB_dC> | t-butylbenzyldC |
| KMTV196FBBC | 8 | AAATTGCGCTAAACTCGATCT<t_BB_dC> | t-butylbenzyldC |
| KMTV194FBBC | 9 | GCAAATTGCGCTAAACTCGAT<t_BB_dC> | t-butylbenzyldC |

TABLE II

5.8s Reverse Primers
Reverse Primers

| Oligo Name | SEQ ID NO: | Sequence | Modifications |
|---|---|---|---|
| KMTV5.8s220RBBA | 10 | TCACACCCATGCTTCTCG<t_BB_dA> | t-butylbenzyldA |
| KMTV5.8s212RBBC | 11 | CATGCTTCTCGACCGAGAT<t_BB_dC> | t-butylbenzyldC |
| KMTV5.8s268RBBA | 12 | TGTTTGTCTTATATATTATTTACTTATTCGCTTAGA<t_BB_dA> | t-butylbenzyldA |
| KMTV270RBBA | 13 | TTTGTCTTATATATTATTTACTTATTCGCTTAGA<t_BB_dA> | t-butylbenzyldA |

TABLE III

5.8s Probes
Probes

| Oligo Name | SEQ ID NO: | Sequence | Modifications |
|---|---|---|---|
| KMTV5.8s167FQ6 | 14 | <F>AACATC<Q>ATGACAGGTTAATCTTTGAATGCAAATTG<P> | P = phosphate, F = th-FAM, Q = BHQ2 |
| KMTV5.8s153FQ6 | 15 | <F>TAACCG<Q>GAGTTGCAAACATCATGACAGG<P> | P = phosphate, F = th-FAM, Q = BHQ2 |
| KMTV5.8s198FQ6 | 16 | <F>ATTGCG<Q>CTAAACTCGATCTCGGTCGA<P> | P = phosphate, F = th-FAM, Q = BHQ2 |

TABLE III-continued

5.8s Probes
Probes

| Oligo Name | SEQ ID NO: | Sequence | Modifications |
|---|---|---|---|
| KMTV5.8s204FQ6 | 17 | <F>CTAAAC<Q>TCGATCTCGGTCG AGAAGCATGG<P> | P = phosphate, F = th-FAM, Q = BHQ2 |
| KMTV5.8s220FQ6 | 18 | <F>TCGAGA<Q>AGCATGGGTGTGA CAGTACTACATCT<P> | P = phosphate, F = th-FAM, Q = BHQ2 |

TABLE IV

18s Forward Primers
Forward Primers

| Oligo Name | SEQ ID NO: | Sequence | Modifications |
|---|---|---|---|
| 16S101BZ | 19 | CGTAGTTGGGATTGACGTTTGTAAT C<t_BZ_dA> | t-benzyldA |
| 16S101BU | 20 | CGTAGTTGGGATTGACGTTTGTAAT C<t_BB_dA> | t-butylbenzyldA |
| 16S103BZ | 21 | GGGAAACTTACCAGGACCAG<t_BZ_ dA> | t-benzyldA |
| 16S103BU | 22 | GGGAAACTTACCAGGACCAG<t_BB_ dA> | t-butylbenzyldA |
| 16S105BZ | 23 | GAAACTTACCAGGACCAGATGTTTT TT<t_BZ_dA> | t-benzyldA |
| 16S105BU | 24 | GAAACTTACCAGGACCAGATGTTTT TT<t_BB_dA> | t-butylbenzyldA |
| 16S107BZ | 25 | CTTGAAGGAATTGACGGAAGGGCA C<t_BZ_dA> | t-benzyldA |
| 16S107BU | 26 | CTTGAAGGAATTGACGGAAGGGCA C<t_BB_dA> | t-butylbenzyldA |
| 16S109BZ | 27 | GCCATTCGACTGAGTGACCTATC<t_ BZ_dA> | t-benzyldA |
| 16S109BU | 28 | GCCATTCGACTGAGTGACCTATC<t_ BB_dA> | t-butylbenzyldA |

TABLE V

18s Reverse Primers
Reverse Primers

| Oligo Name | SEQ ID NO: | Sequence | Modifications |
|---|---|---|---|
| 16S102BZ | 29 | GACTTCTCCTTCCTCTAGATAACGT G<t_BZ_dA> | t-benzyldA |
| 16S102BU | 30 | GACTTCTCCTTCCTCTAGATAACGT G<t_BB_dA> | t-butylbenzyldA |
| 16S104BZ | 31 | TTGCTACCCTCTTCCACCTGCTAA<t_ BZ_dA> | t-benzyldA |
| 16S104BU | 32 | TTGCTACCCTCTTCCACCTGCTAA<t_ BB_dA> | t-butylbenzyldA |
| 16S106BZ | 33 | GCTACCCTCTTCCACCTGCTAAAAT <t_BZ_dC> | t-benzyldC |

TABLE V-continued

18s Reverse Primers
Reverse Primers

| Oligo Name | SEQ ID NO: | Sequence | Modifications |
|---|---|---|---|
| 16S106BU | 34 | GCTACCCTCTTCCACCTGCTAAAAT<t_BB_dC> | t-butylbenzyldC |
| 16S108BZ | 35 | TGAATCAACGCTAGACAGGTCAA<t_BZ_dC> | t-benzyldC |
| 16S108BU | 36 | TGAATCAACGCTAGACAGGTCAA<t_BB_dC> | t-butylbenzyldC |
| 16S110BZ | 37 | AAAAGGCACCAATGGAACTGGTCATT<t_BZ_dA> | t-benzyldA |
| 16S110BU | 38 | AAAAGGCACCAATGGAACTGGTCATT<t_BB_dA> | t-butylbenzyldA |

TABLE VI

18s Probes
Probes

| Oligo Name | SEQ ID NO: | Sequence | Modifications |
|---|---|---|---|
| 16S141FQ6 | 39 | <F>AATCCC<Q>TTGTAAATGTGTGTCAACAACGCA<P> | P = phosphate, F = th-FAM, Q = BHQ2 |
| 16S142FQ6 | 40 | <F>CCACCA<Q>AAAACAATATCCTGAAAGACCCGAAG<P> | P = phosphate, F = th-FAM, Q = BHQ2 |
| 16S144FQ6 | 41 | <F>CCAAAA<Q>ACAATATCCTGAAAGACCCGAAGCCT<P> | P = phosphate, F = th-FAM, Q = BHQ2 |
| 16S146FQ6 | 42 | <F>ACCAAA<Q>AACAATATCCTGAAGACCCGAAGCC<P> | P = phosphate, F = th-FAM, Q = BHQ2 |
| 16S148FQ6 | 43 | <F>CTGCTA<Q>CCCGTGGATATAGTCGCTATCTCTC<P> | P = phosphate, F = th-FAM, Q = BHQ2 |
| 16S143FQ6 | 44 | <F>CTGAGA<Q>GATAGCGACTATATCCACGGGTAGC<P> | P = phosphate, F = th-FAM, Q = BHQ2 |

TABLE VII

PMS1 Forward Primers
Forward Primers

| Oligo Name | SEQ ID NO: | Sequence | Modifications |
|---|---|---|---|
| PMS103BZ | 45 | CCGAGAGATGATTGAGAACGTATTTG<t_BZ_dA> | t-benzyldA |
| PMS103BU | 46 | CCGAGAGATGATTGAGAACGTATTTG<t_BB_dA> | t-butylbenzyldA |
| PMS107BZ | 47 | CACTCCGAGAGATGATTGAGAACGT<t_BZ_dA> | t-benzyldA |
| PMS107BU | 48 | CACTCCGAGAGATGATTGAGAACGT<t_BB_dA> | t-butylbenzyldA |

TABLE VIII

PMS1 Reverse Primers
Reverse Primers

| Oligo Name | SEQ ID NO: | Sequence | Modifications |
|---|---|---|---|
| PMS104BZ | 49 | GCCACTTACATCTTTTCCAAATT<t_BZ_dC> | t-benzyldC |
| PMS104BU | 50 | GCCACTTACATCTTTTCCAAATT<t_BB_dC> | t-butylbenzyldC |
| PMS108BZ | 51 | GTGACACCTTCATCACAAATCATTGAA<t_BZ_dA> | t-benzyldA |
| PMS108BU | 52 | GTGACACCTTCATCACAAATCATTGAA<t_BB_dA> | t-butylbenzyldA |

TABLE IX

PMS1 Probes
Probes

| Oligo Name | SEQ ID NO: | Sequence | Modifications |
|---|---|---|---|
| PMA144FQ6 | 53 | <F>CCACCA<Q>TTTCCAACTCGAATTGTCAAAAGT<P> | P = phosphate, F = th-FAM, Q = BHQ2 |
| PMS146FQ6 | 54 | <F>CCACCA<Q>TTTCCAACTCGAATTGTCAAAAGTGT<P> | P = phosphate, F = th-FAM, Q = BHQ2 |

TABLE X

Mlh1a Forward Primers
Forward Primers

| Oligo Name | SEQ ID NO: | Sequence | Modifications |
|---|---|---|---|
| MLH101BZ | 55 | CTCCTGTATCTATAAATGAAGAGA<t_BZ_dA> | t-benzyldA |
| MLH101BU | 56 | CTCCTGTATCTATAAATGAAGAGA<t_BB_dA> | t-butylbenzyldA |
| MLH103BZ | 57 | GATTTCTGATAATGGCTGTGGAATAA<t_BZ_dA> | t-benzyldA |
| MLH103BU | 58 | GATTTCTGATAATGGCTGTGGAATAA<t_BB_dA> | t-butylbenzyldA |
| MLH105BZ | 59 | GAATTATCTCCTGTATCTATAAATGA<t_BZ_dA> | t-benzyldA |
| MLH105BU | 60 | GAATTATCTCCTGTATCTATAAATGA<t_BB_dA> | t-butylbenzyldA |
| MLH107BZ | 61 | AGTAACAGCAAGTTCACTTTTGT<t_BZ_dC> | t-benzyldC |
| MLH107BU | 62 | AGTAACAGCAAGTTCACTTTTGT<t_BB_dC> | t-butylbenzyldC |
| MLH109BZ | 63 | CAGGTGATATCGCGAAGAACAC<t_BZ_dA> | t-benzyldA |
| MLH109BU | 64 | CAGGTGATATCGCGAAGAACAC<t_BB_dA> | t-butylbenzyldA |

TABLE XI

Mlh1a Reverse Primers
Reverse Primers

| Oligo Name | SEQ ID NO: | Sequence | Modifications |
|---|---|---|---|
| MLH102BZ | 65 | GGAATATTTGATTTTGGAATTTCAG<t_BZ_dA> | t-benzyldA |
| MLH102BU | 66 | GGAATATTTGATTTTGGAATTTCAG<t_BB_dA> | t-butylbenzyldA |
| MLH104BZ | 67 | CCAAATGAACTTTCTTCTGTTTTAG<t_BZ_dA> | t-benzyldA |
| MLH104BU | 68 | CCAAATGAACTTTCTTCTGTTTTAG<t_BB_dA> | t-butylbenzyldA |
| MLH106BZ | 69 | ATTTGATTTTGGAATTTCAGAGTTTT<t_BZ_dC> | t-benzyldC |
| MLH106BU | 70 | ATTTGATTTTGGAATTTCAGAGTTTT<t_BB_dC> | t-butylbenzyldC |
| MLH108BZ | 71 | CTGAAGACTTGGAATAGATGTACTG<t_BZ_dC> | t-benzyldC |
| MLH108BU | 72 | CTGAAGACTTGGAATAGATGTACTG<t_BB_dC> | t-butylbenzyldC |
| MLH110BZ | 73 | GGCATCCTTAATAAAACAAAAGCAA<t_BZ_dA> | t-benzyldA |
| MLH110BU | 74 | GGCATCCTTAATAAAACAAAAGCAA<t_BB_dA> | t-butylbenzyldA |

TABLE XII

Mlh1a Probes
Probes

| Oligo Name | SEQ ID NO: | Sequence | Modifications |
|---|---|---|---|
| MLH141FQ6 | 75 | <F>AAAATC<Q>CAAGAAAAAGAGC AAGAAGAAATCCT<P> | P = phosphate, F = th-FAM, Q = BHQ2 |
| MLH142FQ6 | 76 | <F>CACCTC<Q>TGAATCCAAATGTA GTTACGTTCCTT<P> | P = phosphate, F = th-FAM, Q = BHQ2 |
| MLH144FQ6 | 77 | <F>CTTGCT<Q>CTTTTTCTTGGATT TTCTGTATCTGA<P> | P = phosphate, F = th-FAM, Q = BHQ2 |
| MLH146FQ6 | 78 | <F>TTCAAA<Q>CCAATCAAACCAA CAAAAGAATGAGC<P> | P = phosphate, F = th-FAM, Q = BHQ2 |
| MLH148FQ6 | 79 | <F>AAAACC<Q>GCTGATTCTTTGA GTTGTTTTTGGC<P> | P = phosphate, F = th-FAM, Q = BHQ2 |

TABLE XIII

CRN Forward Primers
Forward Primers

| Oligo Name | SEQ ID NO: | Sequence | Modifications |
|---|---|---|---|
| CRN101BZ | 80 | GCAATCTGGGATCTCAACAAGGAA<t_BZ_dA> | t-benzyldA |
| CRN101BU | 81 | GCAATCTGGGATCTCAACAAGGAA<t_BB_dA> | t-butylbenzyldA |

TABLE XIII-continued

CRN Forward Primers
Forward Primers

| Oligo Name | SEQ ID NO: | Sequence | Modifications |
| --- | --- | --- | --- |
| CRN103BZ | 82 | TTTCATCGGACAGGGCAATC<t_BZ_dC> | t-benzyldC |
| CRN103BU | 83 | TTTCATCGGACAGGGCAATC<t_BB_dC> | t-butylbenzyldC |
| CRN105BZ | 84 | GAGGGACCACAAGAAGAAGTCGTTC<t_BZ_dA> | t-benzyldA |
| CRN105BU | 85 | GAGGGACCACAAGAAGAAGTCGTTC<t_BB_dA> | t-butylbenzyldA |
| CRN107BZ | 86 | GACGAGGGACCACAAGAAGAAGT<t_BZ_dC> | t-benzyldC |
| CRN107BU | 87 | GACGAGGGACCACAAGAAGAAGT<t_BB_dC> | t-butylbenzyldC |
| CRN109BZ | 88 | CAGAGATCATCCAGCCAGAT<t_BZ_dC> | t-benzyldC |
| CRN109BU | 89 | CAGAGATCATCCAGCCAGAT<t_BB_dC> | t-butylbenzyldC |

TABLE XIV

CRN Reverse Primers
Reverse Primers

| Oligo Name | SEQ ID NO: | Sequence | Modifications |
| --- | --- | --- | --- |
| CRN102BZ | 90 | GGTTGTAATCTGGAAGGTCGAGA<t_BZ_dA> | t-benzyldA |
| CRN102BU | 91 | GGTTGTAATCTGGAAGGTCGAGA<t_BB_dA> | t-butylbenzyldA |
| CRN104BZ | 92 | AACGTCAGGAACATCCCAAAGG<t_BZ_dC> | t-benzyldC |
| CRN104BU | 93 | AACGTCAGGAACATCCCAAAGG<t_BB_dC> | t-butylbenzyldC |
| CRN106BZ | 94 | GCGAGTTGGCTTATCAAGGTTCATGA<t_BZ_dA> | t-benzyldA |
| CRN106BU | 95 | GCGAGTTGGCTTATCAAGGTTCATGA<t_BB_dA> | t-butylbenzyldA |
| CRN108BZ | 96 | GTTGATTGGATAGCGAGTTGG<t_BZ_dC> | t-benzyldC |
| CRN108BU | 97 | GTTGATTGGATAGCGAGTTGG<t_BB_dC> | t-butylbenzyldC |
| CRN110BZ | 98 | CTCGTCGACAACTTCCTCCT<t_BZ_dC> | t-benzyldC |
| CRN110BU | 99 | CTCGTCGACAACTTCCTCCT<t_BZ_dC> | t-butylbenzyldC |

TABLE XV

CRN Probes
Probes

| Oligo Name | SEQ ID NO: | Sequence | Modifications |
|---|---|---|---|
| CRN141FQ6 | 100 | <F>CCAAGA<Q>CTCAACATTCAAC TCATTATCTAACG<P> | P = phosphate, F = th-FAM, Q = BHQ2 |
| CRN143FQ6 | 101 | <F>ACATCA<Q>CATACTCACCACAT AATCCAAATCT<P> | P = phosphate, F = th-FAM, Q = BHQ2 |
| CRN142FQ6 | 102 | <F>ACAATG<Q>CCAACTGGAAGAT AAGTAAAGTAGT<P> | P = phosphate, F = th-FAM, Q = BHQ2 |
| CRN144FQ6 | 103 | <F>ACAATG<Q>CCAACTGGAAGAT AAGTAAAGTAGTT<P> | P = phosphate, F = th-FAM, Q = BHQ2 |
| CRN146FQ6 | 104 | <F>TTGGAA<Q>GATGGGATTTGTC AACTGTCAATCTG<P> | P = phosphate, F = th-FAM, Q = BHQ2 |
| CRN148FQ6 | 105 | <F>TTGGAA<Q>GATGGGATTTGTC AACTGTCAATCT<P> | P = phosphate, F = th-FAM, Q = BHQ2 |

In one embodiment, the above described sets of primers and probes are used in order to provide for detection of TV in a biological sample suspected of containing TV. The sets of primers and probes may comprise or consist of the primers and probes specific for the nucleic acid sequences of the 5.8s gene, 18s gene, PMS1 gene, Mlh1a gene and CRN gene comprising or consisting of the nucleic acid sequences of SEQ ID NOs: 1-105. In another embodiment, the primers and probes for the target TV genes comprise or consist of a functionally active variant of any of the primers and probes of SEQ ID NOs: 1-105.

A functionally active variant of any of the primers and/or probes of SEQ ID NOs: 1-105 may be identified by using the primers and/or probes in the disclosed methods. A functionally active variant of a primer and/or probe of any of the SEQ ID NOs: 1-105 pertains to a primer and/or probe which provides a similar or higher specificity and sensitivity in the described method or kit as compared to the respective sequence of SEQ ID NOs: 1-105.

The variant may, e.g., vary from the sequence of SEQ ID NOs: 1-105 by one or more nucleotide additions, deletions or substitutions such as one or more nucleotide additions, deletions or substitutions at the 5' end and/or the 3' end of the respective sequence of SEQ ID NOs: 1-105. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the target TV gene, e.g. the 5.8s gene, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length). In some embodiments oligonucleotide primers are 40 or fewer nucleotides in length.

In addition to a set of primers, the methods may use one or more probes in order to detect the presence or absence of TV. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to an target TV gene nucleic acid. A "probe" can be referred to as a "detection probe" meaning that it detects the target nucleic acid.

In some embodiments, the described target TV gene probes can be labeled with at least one fluorescent label. In one embodiment, the target TV gene probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs: 14-18, 39-44, 53-54, 75-79, and 100-105.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of target TV gene primers and probes nucleic acid molecules. Constructs can be used, for example, as control template nucleic acid molecules. Vectors suitable for use are commercially available and/or produced by recombinant nucleic acid technology methods routine in the art. Target TV gene nucleic acid molecules can be obtained, for example, by chemical synthesis, direct cloning from TV, or by PCR amplification.

Constructs suitable for use in the methods typically include, in addition to the target TV gene nucleic acid molecules (e.g., a nucleic acid molecule that contains one or more sequences of SEQ ID NOs: 1-105), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing target TV gene nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described target TV gene nucleic acid sequences (e.g., SEQ ID NOs: 1-13, 19-38, 45-52, 55-74, and 80-99). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target TV gene nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ nucleic acid such as RNA or DNA (cDNA). The template nucleic acid need not be purified; it may be a minor fraction of a complex mixture, such as nucleic acid contained in human cells. Nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, protozoa viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µgprotodenatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, a oligonucleotide probe can contain a donor fluorescent moiety and a corresponding quencher, which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced there between.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of TV

The present disclosure provides methods for detecting the presence or absence of TV in a biological or non-biological sample. Methods provided avoid problems of sample contamination, false negatives, and false positives. The methods include performing at least one cycling step that includes amplifying a portion of target nucleic acid molecules from a sample using one or more pairs of primers, and a FRET detecting step. Multiple cycling steps are performed, preferably in a thermocycler. Methods can be performed using the primers and probes to detect the presence of TV, and the detection of the target TV gene indicates the presence of TV in the sample.

As described herein, amplification products can be detected using labeled hybridization probes that take advantage of FRET technology. One FRET format utilizes TaqMan® technology to detect the presence or absence of an amplification product, and hence, the presence or absence of TV. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of TV in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of TV genomes). If amplification of target nucleic acid occurs and an amplification product is produced, the step of hybridizing results in a detectable signal based upon FRET between the members of the pair of probes.

Generally, the presence of FRET indicates the presence of TV in the sample, and the absence of FRET indicates the absence of TV in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of a TV infection.

Representative biological samples that can be used in practicing the methods include, but are not limited to respiratory specimens, fecal specimens, blood specimens, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release TV nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the probes from the amplification products can confirm the presence or absence of TV in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos.

5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present disclosure are not limited by the configuration of one or more commercially available instruments.

Articles of Manufacture/Kits

Embodiments of the present disclosure further provide for articles of manufacture, compositions or kits to detect TV. An article of manufacture can include primers and probes used to detect the target TV gene, together with suitable packaging materials. Compositions can include primers used to amplify the target TV gene. In certain embodiments compositions can also comprise probes for detecting the target TV gene. Representative primers and probes for detection of TV are capable of hybridizing to target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the probes. Examples of suitable FRET donor fluorescent moieties and corresponding acceptor fluorescent moieties are provided above.

Articles of manufacture can also contain a package insert or package label having instructions thereon for using the primers and probes to detect TV in a sample. Articles of manufacture and compositions may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples, tables and figures are provided to aid the understanding of the subject matter, the true scope of which is set forth in the appended claims. It is understood that modifications can be made in the procedures set forth without departing from the spirit of the invention.

Example I

Target selection for TV was the result of a comprehensive search of the public sequence database, as well as a literature search for TV targets with a potential to discriminate against the nearest neighbors, *Trichomonas tenax* and *Pentatrichomonas hominis*. Multiple targets from the public sequence database were analyzed in the target selection process of the design phase, but all showed cross reactivity with *T. tenax* and *P. hominis*. The sequences in the public database are complicated by "bulk" sequence data from multicopy targets. BLAST analysis of the chosen oligonucleotides indicated that the only significant cross reactivity will be with *Trichomonas tenax*.

Real-time PCR detection of TV were performed using either the Cobas® 4800 system or the Cobas® 6800/8800 systems platforms (Roche Molecular Systems, Inc., Pleasanton, Calif.). The final concentrations of the amplification reagents are shown below:

TABLE XVI

| PCR Amplification Reagents | |
| --- | --- |
| Master Mix Component | Final Conc (50 uL) |
| DMSO | 0-5.4 % |
| NaN3 | 0.027-0.030 % |
| Potassium acetate | 120.0 mM |
| Glycerol | 3.0 % |
| Tween 20 | 0.02 % |
| EDTA | 0-43.9 uM |
| Tricine | 60.0 mM |
| Aptamer | 0.18-0.22 uM |
| UNG Enzyme | 5.0-10.0 U |
| Z05-SP-PZ Polymerase | 30.0-45.0 U |
| dATP | 400.0-521.70 uM |
| dCTP | 400.0-521.70 uM |
| dGTP | 400.0-521.70 uM |
| dUTP | 800.0-1043.40 uM |
| Forward primer oligonucleotides | 0.15-0.50 μM |
| Reverse primer oligonucleotides | 0.15-0.50 μM |
| Probe oligonucleotides | 0.10 μM |
| Manganese Acetate | 3.30-3.80 mM |

The following table shows the typical thermoprofile used for PCR amplification reaction:

TABLE XVII

PCR Thermoprofile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
| | 94 | None | 00:00:05 | 4.4 | | |
| | 55 | None | 00:02:00 | 2.2 | | |
| | 60 | None | 00:06:00 | 4.4 | | |
| | 65 | None | 00:04:00 | 4.4 | | |
| 1st Measurement | 95 | None | 00:00:05 | 4.4 | 5 | Quantification |
| | 55 | Single | 00:00:30 | 2.2 | | |
| 2nd Measurment | 91 | None | 00:00:05 | 4.4 | 45 | Quantification |
| | 58 | Single | 00:00:25 | 2.2 | | |
| Cooling | 40 | None | 00:02:00 | 2.2 | 1 | None |

Figure 2:
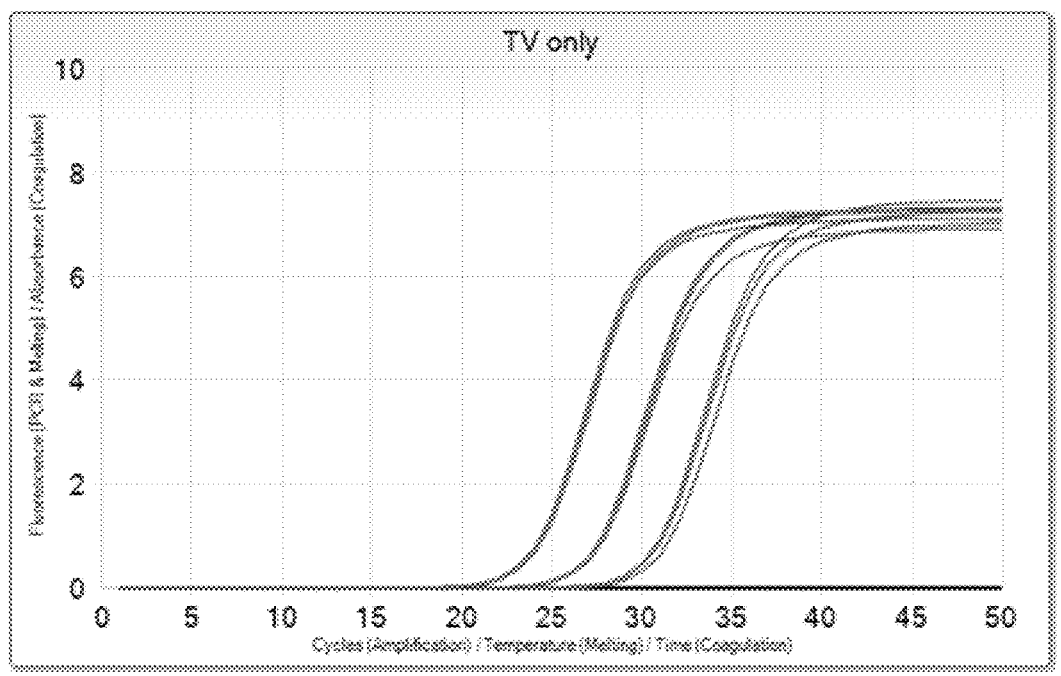
FIG. 2 shows PCR growth curves of a real-time PCR experiment in the presence of various concentrations of genomic *T. vaginalis* DNA template (present in 1000 [black], 100 [light grey] and 10 [grey] genomic equivalent concentrations per PCR reaction).

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C. FIG. 2 depicts a typical amplification experiment where PCR growth curves are shown in various concentrations of genomic TV template DNA.

The amplification and detection of the target TV genes, 5.8s rRNA, 18s rRNA, PMS1, Mlh1a and CRN were performed using the conditions described above. The results of the experiments using several selected oligonucleotide primers and probes against genomic TV DNA present at a concentration of either 10 genomic equivalent/PCR (5.8s rRNA) or 1000 genomic equivalent/PCR (18s rRNA, PMS1, Mlh1a, CRN) are shown below as Ct values (threshold cycle) for the amplification reactions.

TABLE XVIII

Amplification and Detection of target TV genes

| Target TV Gene | Forward primer SEQ ID NO | Reverse primer SEQ ID NO | Probe SEQ ID NO | Ct values 10 ge/PCR of TV |
|---|---|---|---|---|
| 5.8s rRNA | 3 | 12 | 16 | 27.3 |
| | 3 | 12 | 17 | 30.1 |
| | 3 | 12 | 18 | 27.5 |
| | 6 | 12 | 18 | 28.5 |
| | 7 | 12 | 18 | 28.1 |
| | 9 | 12 | 18 | 28.0 |
| 18s rRNA | 21 | 31 | 40 | 24.9 |
| | 22 | 32 | 40 | 25.4 |
| PMS1 | 45 | 49 | 54 | 31.6 |
| | 46 | 50 | 54 | 32.0 |
| | 47 | 51 | 54 | 32.3 |
| | 48 | 52 | 54 | 32.2 |
| Mlh1a | 57 | 67 | 76 | 32.7 |
| | 58 | 68 | 76 | 33.4 |
| | 63 | 73 | 79 | 32.5 |
| | 64 | 74 | 79 | 32.9 |
| CRN | 80 | 90 | 100 | 34.6 |
| | 81 | 91 | 100 | 35.0 |
| | 82 | 92 | 101 | 33.5 |
| | 83 | 93 | 101 | 33.5 |

Example 2

The amplification and detection of the TV 5.8s rRNA gene was performed as described in Example 1 with the exception that genomic template DNA for *Mycoplasma genitalium* (MG) was included in the PCR assay together with primers and probes that can amplify and detect MG. In this experiment, primers and probes, disclosed in U.S. Provisional Application No. 62/342,519, that hybridize to the conserved region A of the mgpB gene (mgpB) and to the variable region EF of the mgpB gene (MgPar) were used.

Figure 3:
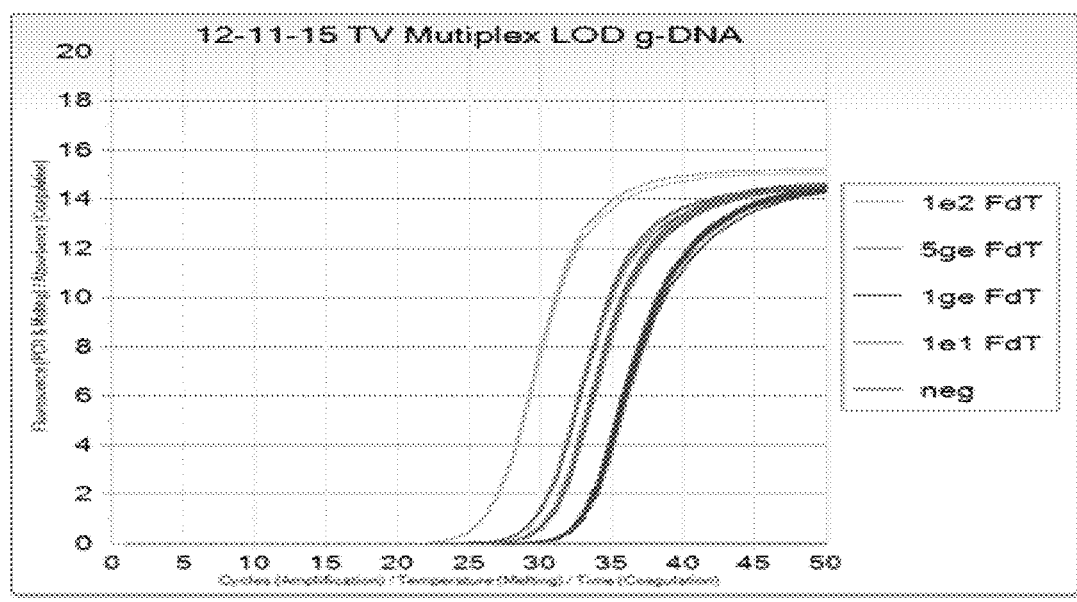
FIG. 3 shows PCR growth curves of a real-time PCR experiment with concentrations of genomic *T. vaginalis* DNA template present in 100, 10, 5 and 1 genomic equivalent concentrations per PCR reaction (ge/PCR), in a co-amplification with internal control standard and *Mycoplasma genitalium* DNA template at 10 ge/PCR.
Figure 4:
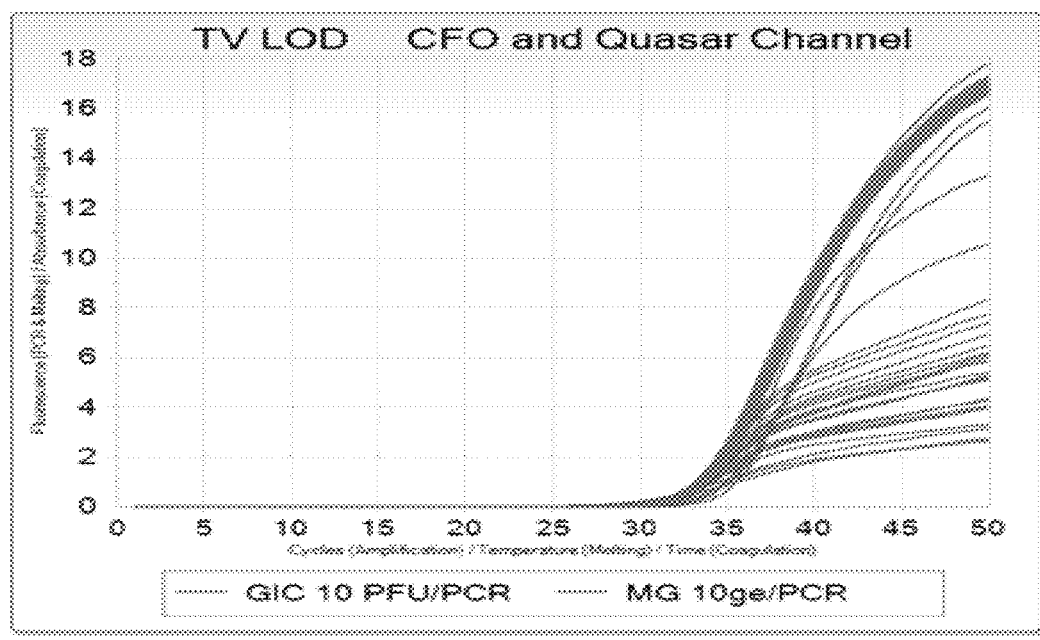
FIG. 4 shows PCR growth curves of the same real-time PCR experiment as shown on FIG. 3 with the amplification of the internal control standard and *Mycoplasma genitalium* DNA template at 10 ge/PCR.

TV Limit of Detection (LOD) was tested at 100, 10, 5 and 1 genomic equivalent concentrations per PCR reaction (ge/PCR), in a co-amplification with internal control standard and MG at 10 ge/PCR. The results are shown on FIGS. 3 and 4. All levels of TV were detected with no dropouts, and TV LOD is determined to be <1 ge/PCR.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of specifically amplifying and detecting Trichomonas vaginalis (TV) in a sample by discriminating against Trichomonas tenax and Pentatrichomonas homini the method comprising:
    performing an amplifying step comprising contacting the sample with a set of target TV gene primers to produce an amplification product if a target TV gene nucleic acid is present in the sample, wherein the target TV gene is the 5.8s ribosomal RNA gene;
    performing a hybridizing step comprising contacting the amplification product with one or more detectable target TV gene probes; and
    detecting the presence or absence of the amplification product, wherein the presence of the amplification product is indicative of the presence of TV in the sample and wherein the absence of the amplification product is indicative of the absence of TV in the sample;
    wherein the set of target TV gene primers comprise a first primer consisting of SEQ ID NO: 3 and a second primer consisting of SEQ ID NO: 12; and
    wherein the detectable target TV gene probes comprises a third oligonucleotide sequence consisting of SEQ ID NO: 18;
    and wherein the method does not detect Trichomonas tenax and Pentatrichomonas hominis.

2. The method of claim 1, wherein:
    the hybridizing step comprises contacting the amplification product with the detectable target TV gene probe that is labeled with a donor fluorescent moiety and a corresponding acceptor moiety; and
    the detecting step comprises detecting the presence or absence of fluorescence resonance energy transfer (FRET) between the donor fluorescent moiety and the acceptor moiety of the probe, wherein the presence or absence of fluorescence is indicative of the presence or absence of TV in the sample.

3. The method of claim 2, wherein said amplification step employs a polymerase enzyme having 5' to 3' nuclease activity.

4. The method of claim 2, wherein the donor fluorescent moiety and the corresponding acceptor moiety are within no more than 8-20 nucleotides of each other on the probe.

5. The method of claim 2, wherein the acceptor moiety is a quencher.

* * * * *

SEQUENCE LISTING

<160> NUMBER OF SEQ ID NOS: 105

<210> SEQ ID NO 1
<211> LENGTH: 24
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (24)..(24)
<223> OTHER INFORMATION: t-butylbenzyldC

<400> SEQUENCE: 1
ccaagtctct aagcaatgga tgtc                                              24

<210> SEQ ID NO 2
<211> LENGTH: 21
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (21)..(21)
<223> OTHER INFORMATION: t-butylbenzyldC

<400> SEQUENCE: 2
aagcaatgga tgtcttggct c                                                 21

<210> SEQ ID NO 3
<211> LENGTH: 24
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (24)..(24)
<223> OTHER INFORMATION: t-butylbenzyldC

<400> SEQUENCE: 3
tgttaagtaa ccggagttgc aaac                                              24

<210> SEQ ID NO 4
<211> LENGTH: 22
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (22)..(22)
<223> OTHER INFORMATION: t-butylbenzyldC

<400> SEQUENCE: 4
ttaagtaacc ggagttgcaa ac                                                22

<210> SEQ ID NO 5
<211> LENGTH: 23
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (23)..(23)
<223> OTHER INFORMATION: t-butylbenzyldC

<400> SEQUENCE: 5

-continued caaattgcgc taaactcgat ctc                                         23

<210> SEQ ID NO 6
<211> LENGTH: 20
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (20)..(20)
<223> OTHER INFORMATION: t-butylbenzyldA

<400> SEQUENCE: 6
ctaaactcga tctcggtcga                                             20

<210> SEQ ID NO 7
<211> LENGTH: 20
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (20)..(20)
<223> OTHER INFORMATION: t-butylbenzyldC

<400> SEQUENCE: 7
cgctaaactc gatctcggtc                                             20

<210> SEQ ID NO 8
<211> LENGTH: 22
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (22)..(22)
<223> OTHER INFORMATION: t-butylbenzyldC

<400> SEQUENCE: 8
aaattgcgct aaactcgatc tc                                          22

<210> SEQ ID NO 9
<211> LENGTH: 22
<212> TYPE: DNA
<213> ORGANISM: Artificial Sequence
<220> FEATURE:
<223> OTHER INFORMATION: 5.8s forward primer
<220> FEATURE:
<221> NAME/KEY: modified_base
<222> LOCATION: (22)..(22)
<223> OTHER INFORMATION: t-butylbenzyldC

<400> SEQUENCE: 9
gcaaattgcg ctaaactcga tc                                          22

<210> SEQ ID NO 10
<211> LENGTH: 19
<212> TYPE: DNA
<213> ORGANISM: Artificial Sequence
<220> FEATURE:
<223> OTHER INFORMATION: 5.8s reverse primer
<220> FEATURE:
<221> NAME/KEY: modified_base
<222> LOCATION: (19)..(19)
<223> OTHER INFORMATION: t-butylbenzyldA

```
<400> SEQUENCE: 10
tcacacccat gcttctcga                                             19

<210> SEQ ID NO 11
<211> LENGTH: 20
<212> TYPE: DNA
<213> ORGANISM: Artificial Sequence
<220> FEATURE:
<223> OTHER INFORMATION: 5.8s reverse primer
<220> FEATURE:
<221> NAME/KEY: modified_base
<222> LOCATION: (20)..(20)
<223> OTHER INFORMATION: t-butylbenzyldC

<400> SEQUENCE: 11
catgcttctc gaccgagatc                                            20

<210> SEQ ID NO 12
<211> LENGTH: 37
<212> TYPE: DNA
<213> ORGANISM: Artificial Sequence
<220> FEATURE:
<223> OTHER INFORMATION: 5.8s reverse primer
<220> FEATURE:
<221> NAME/KEY: modified_base
<222> LOCATION: (37)..(37)
<223> OTHER INFORMATION: t-butylbenzyldA

<400> SEQUENCE: 12
tgtttgtctt atatattatt tacttattcg cttagaa                         37

<210> SEQ ID NO 13
<211> LENGTH: 35
<212> TYPE: DNA
<213> ORGANISM: Artificial Sequence
<220> FEATURE:
<223> OTHER INFORMATION: 5.8s reverse primer
<220> FEATURE:
<221> NAME/KEY: modified_base
<222> LOCATION: (35)..(35)
<223> OTHER INFORMATION: t-butylbenzyldA

<400> SEQUENCE: 13
tttgtcttat atattattta cttattcgct tagaa                           35

<210> SEQ ID NO 14
<211> LENGTH: 35
<212> TYPE: DNA
<213> ORGANISM: Artificial Sequence
<220> FEATURE:
<223> OTHER INFORMATION: 5.8s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3'  phosphate
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 14
aacatcatga caggttaatc tttgaatgca aattg                           35

<210> SEQ ID NO 15
```

-continued

```
<211> LENGTH: 28
<212> TYPE: DNA
<213> ORGANISM: Artificial Sequence
<220> FEATURE:
<223> OTHER INFORMATION: 5.8s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 15
taaccggagt tgcaaacatc atgacagg                                          28

<210> SEQ ID NO 16
<211> LENGTH: 26
<212> TYPE: DNA
<213> ORGANISM: Artificial Sequence
<220> FEATURE:
<223> OTHER INFORMATION: 5.8s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 16
attgcgctaa actcgatctc ggtcga                                            26

<210> SEQ ID NO 17
<211> LENGTH: 29
<212> TYPE: DNA
<213> ORGANISM: Artificial Sequence
<220> FEATURE:
<223> OTHER INFORMATION: 5.8s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 17
ctaaactcga tctcggtcga gaagcatgg                                         29

<210> SEQ ID NO 18
<211> LENGTH: 32
<212> TYPE: DNA
<213> ORGANISM: Artificial Sequence
<220> FEATURE:
<223> OTHER INFORMATION: 5.8s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
```

```
<222> LOCATION: (6)..(7)
<223> OTHER INFORMATION: BHQ-2

<400> SEQUENCE: 18
tcgagaagca tgggtgtgac agtactacat ct                                   32

<210> SEQ ID NO 19
<211> LENGTH: 27
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (27)..(27)
<223> OTHER INFORMATION: t-benzyldA

<400> SEQUENCE: 19
cgtagttggg attgacgttt gtaatca                                          27

<210> SEQ ID NO 20
<211> LENGTH: 27
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (27)..(27)
<223> OTHER INFORMATION: t-butylbenzyldA

<400> SEQUENCE: 20
cgtagttggg attgacgttt gtaatca                                          27

<210> SEQ ID NO 21
<211> LENGTH: 21
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (21)..(21)
<223> OTHER INFORMATION: t-benzyldA

<400> SEQUENCE: 21
gggaaactta ccaggaccag a                                                21

<210> SEQ ID NO 22
<211> LENGTH: 21
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (21)..(21)
<223> OTHER INFORMATION: t-butylbenzyldA

<400> SEQUENCE: 22
gggaaactta ccaggaccag a                                                21

<210> SEQ ID NO 23
<211> LENGTH: 28
<212> TYPE: DNA
<213> ORGANISM: Artificial Sequence
<220> FEATURE:
<223> OTHER INFORMATION: 18s forward primer
<220> FEATURE:
```

```
<221> NAME/KEY: modified_base
<222> LOCATION: (28)..(28)
<223> OTHER INFORMATION: t-benzyldA

<400> SEQUENCE: 23
gaaacttacc aggaccagat gtttttta                                          28

<210> SEQ ID NO 24
<211> LENGTH: 28
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (28)..(28)
<223> OTHER INFORMATION: t-butylbenzyldA

<400> SEQUENCE: 24
gaaacttacc aggaccagat gtttttta                                          28

<210> SEQ ID NO 25
<211> LENGTH: 26
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (26)..(26)
<223> OTHER INFORMATION: t-benzyldA

<400> SEQUENCE: 25
cttgaaggaa ttgacggaag ggcaca                                            26

<210> SEQ ID NO 26
<211> LENGTH: 26
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (26)..(26)
<223> OTHER INFORMATION: t-butylbenzyldA

<400> SEQUENCE: 26
cttgaaggaa ttgacggaag ggcaca                                            26

<210> SEQ ID NO 27
<211> LENGTH: 24
<212> TYPE: DNA
<213> ORGANISM: Artificial Sequence
<220> FEATURE:
<223> OTHER INFORMATION: 18s forward primer
<220> FEATURE:
<221> NAME/KEY: modified_base
<222> LOCATION: (24)..(24)
<223> OTHER INFORMATION: t-benzyldA

<400> SEQUENCE: 27
gccattcgac tgagtgacct atca                                              24

<210> SEQ ID NO 28
<211> LENGTH: 24
<212> TYPE: DNA
<213> ORGANISM: Artificial Sequence
<220> FEATURE:
<223> OTHER INFORMATION: 18s forward primer
```

```
<220> FEATURE:
<221> NAME/KEY: modified_base
<222> LOCATION: (24)..(24)
<223> OTHER INFORMATION: t-butylbenzyldA

<400> SEQUENCE: 28
gccattcgac tgagtgacct atca                                          24

<210> SEQ ID NO 29
<211> LENGTH: 27
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (27)..(27)
<223> OTHER INFORMATION: t-benzyldA

<400> SEQUENCE: 29
gacttctcct tcctctagat aacgtga                                       27

<210> SEQ ID NO 30
<211> LENGTH: 27
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (27)..(27)
<223> OTHER INFORMATION: t-butylbenzyldA

<400> SEQUENCE: 30
gacttctcct tcctctagat aacgtga                                       27

<210> SEQ ID NO 31
<211> LENGTH: 25
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (25)..(25)
<223> OTHER INFORMATION: t-benzyldA

<400> SEQUENCE: 31
ttgctaccct cttccacctg ctaaa                                         25

<210> SEQ ID NO 32
<211> LENGTH: 25
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (25)..(25)
<223> OTHER INFORMATION: t-butylbenzyldA

<400> SEQUENCE: 32
ttgctaccct cttccacctg ctaaa                                         25

<210> SEQ ID NO 33
<211> LENGTH: 26
<212> TYPE: DNA
<213> ORGANISM: Artificial Sequence
<220> FEATURE:
```

<223> OTHER INFORMATION: 18s reverse primer
<220> FEATURE:
<221> NAME/KEY: modified_base
<222> LOCATION: (26)..(26)
<223> OTHER INFORMATION: t-benzyldC

<400> SEQUENCE: 33
gctaccctct tccacctgct aaaatc                                              26

<210> SEQ ID NO 34
<211> LENGTH: 26
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (26)..(26)
<223> OTHER INFORMATION: t-butylbenzyldC

<400> SEQUENCE: 34
gctaccctct tccacctgct aaaatc                                              26

<210> SEQ ID NO 35
<211> LENGTH: 24
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (24)..(24)
<223> OTHER INFORMATION: t-benzyldC

<400> SEQUENCE: 35
tgaatcaacg ctagacaggt caac                                                24

<210> SEQ ID NO 36
<211> LENGTH: 24
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (24)..(24)
<223> OTHER INFORMATION: t-butylbenzyldC

<400> SEQUENCE: 36
tgaatcaacg ctagacaggt caac                                                24

<210> SEQ ID NO 37
<211> LENGTH: 27
<212> TYPE: DNA
<213> ORGANISM: Artificial Sequence
<220> FEATURE:
<223> OTHER INFORMATION: 18s reverse primer
<220> FEATURE:
<221> NAME/KEY: modified_base
<222> LOCATION: (27)..(27)
<223> OTHER INFORMATION: t-benzyldA

<400> SEQUENCE: 37
aaaaggcacc aatggaactg gtcatta                                             27

<210> SEQ ID NO 38
<211> LENGTH: 27
<212> TYPE: DNA
<213> ORGANISM: Artificial Sequence

```
<220> FEATURE:
<223> OTHER INFORMATION: 18s reverse primer
<220> FEATURE:
<221> NAME/KEY: modified_base
<222> LOCATION: (27)..(27)
<223> OTHER INFORMATION: t-butylbenzyldA

<400> SEQUENCE: 38
aaaaggcacc aatggaactg gtcatta                                           27

<210> SEQ ID NO 39
<211> LENGTH: 30
<212> TYPE: DNA
<213> ORGANISM: Artificial Sequence
<220> FEATURE:
<223> OTHER INFORMATION: 18s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 39
aatcccttgt aaatgtgtgt caacaacgca                                        30

<210> SEQ ID NO 40
<211> LENGTH: 32
<212> TYPE: DNA
<213> ORGANISM: Artificial Sequence
<220> FEATURE:
<223> OTHER INFORMATION: 18s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 40
ccaccaaaaa caatatcctg aaagacccga ag                                     32

<210> SEQ ID NO 41
<211> LENGTH: 32
<212> TYPE: DNA
<213> ORGANISM: Artificial Sequence
<220> FEATURE:
<223> OTHER INFORMATION: 18s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 41
ccaaaaacaa tatcctgaaa gacccgaagc ct                                     32

<210> SEQ ID NO 42
```

```
<211> LENGTH: 32
<212> TYPE: DNA
<213> ORGANISM: Artificial Sequence
<220> FEATURE:
<223> OTHER INFORMATION: 18s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 42
accaaaaaca atatcctgaa agacccgaag cc                                      32

<210> SEQ ID NO 43
<211> LENGTH: 31
<212> TYPE: DNA
<213> ORGANISM: Artificial Sequence
<220> FEATURE:
<223> OTHER INFORMATION: 18s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 43
ctgctacccg tggatatagt cgctatctct c                                       31

<210> SEQ ID NO 44
<211> LENGTH: 31
<212> TYPE: DNA
<213> ORGANISM: Artificial Sequence
<220> FEATURE:
<223> OTHER INFORMATION: 18s probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 44
ctgagagata gcgactatat ccacgggtag c                                       31

<210> SEQ ID NO 45
<211> LENGTH: 27
<212> TYPE: DNA
<213> ORGANISM: Artificial Sequence
<220> FEATURE:
<223> OTHER INFORMATION: PMS1 forward primer
<220> FEATURE:
<221> NAME/KEY: modified_base
<222> LOCATION: (27)..(27)
<223> OTHER INFORMATION: t-benzyldA

<400> SEQUENCE: 45
ccgagagatg attgagaacg tatttga                                            27
```

<210> SEQ ID NO 46
<211> LENGTH: 27
<212> TYPE: DNA
<213> ORGANISM: Artificial Sequence
<220> FEATURE:
<223> OTHER INFORMATION: PMS1 forward primer
<220> FEATURE:
<221> NAME/KEY: modified_base
<222> LOCATION: (27)..(27)
<223> OTHER INFORMATION: t-butylbenzyldA

<400> SEQUENCE: 46
ccgagagatg attgagaacg tatttga                    27

<210> SEQ ID NO 47
<211> LENGTH: 26
<212> TYPE: DNA
<213> ORGANISM: Artificial Sequence
<220> FEATURE:
<223> OTHER INFORMATION: PMS1 forward primer
<220> FEATURE:
<221> NAME/KEY: modified_base
<222> LOCATION: (26)..(26)
<223> OTHER INFORMATION: t-benzyldA

<400> SEQUENCE: 47
cactccgaga gatgattgag aacgta                     26

<210> SEQ ID NO 48
<211> LENGTH: 26
<212> TYPE: DNA
<213> ORGANISM: Artificial Sequence
<220> FEATURE:
<223> OTHER INFORMATION: PMS1 forward primer
<220> FEATURE:
<221> NAME/KEY: modified_base
<222> LOCATION: (26)..(26)
<223> OTHER INFORMATION: t-butylbenzyldA

<400> SEQUENCE: 48
cactccgaga gatgattgag aacgta                     26

<210> SEQ ID NO 49
<211> LENGTH: 24
<212> TYPE: DNA
<213> ORGANISM: Artificial Sequence
<220> FEATURE:
<223> OTHER INFORMATION: PMS1 reverse primer
<220> FEATURE:
<221> NAME/KEY: modified_base
<222> LOCATION: (24)..(24)
<223> OTHER INFORMATION: t-benzyldC

<400> SEQUENCE: 49
gccacttaca tcttttccaa attc                       24

<210> SEQ ID NO 50
<211> LENGTH: 24
<212> TYPE: DNA
<213> ORGANISM: Artificial Sequence
<220> FEATURE:
<223> OTHER INFORMATION: PMS1 reverse primer
<220> FEATURE:
<221> NAME/KEY: modified_base
<222> LOCATION: (24)..(24)
<223> OTHER INFORMATION: t-butylbenzyldC

<400> SEQUENCE: 50
gccacttaca tcttttccaa attc					24

<210> SEQ ID NO 51
<211> LENGTH: 28
<212> TYPE: DNA
<213> ORGANISM: Artificial Sequence
<220> FEATURE:
<223> OTHER INFORMATION: PMS1 reverse primer
<220> FEATURE:
<221> NAME/KEY: modified_base
<222> LOCATION: (28)..(28)
<223> OTHER INFORMATION: t-benzyldA

<400> SEQUENCE: 51
gtgacaccct tcatcacaaat cattgaaa					28

<210> SEQ ID NO 52
<211> LENGTH: 28
<212> TYPE: DNA
<213> ORGANISM: Artificial Sequence
<220> FEATURE:
<223> OTHER INFORMATION: PMS1 reverse primer
<220> FEATURE:
<221> NAME/KEY: modified_base
<222> LOCATION: (28)..(28)
<223> OTHER INFORMATION: t-butylbenzyldA

<400> SEQUENCE: 52
gtgacaccct tcatcacaaat cattgaaa					28

<210> SEQ ID NO 53
<211> LENGTH: 30
<212> TYPE: DNA
<213> ORGANISM: Artificial Sequence
<220> FEATURE:
<223> OTHER INFORMATION: PMS1 probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 53
ccaccatttc caactcgaat tgtcaaaagt					30

<210> SEQ ID NO 54
<211> LENGTH: 32
<212> TYPE: DNA
<213> ORGANISM: Artificial Sequence
<220> FEATURE:
<223> OTHER INFORMATION: PMS1 probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 54
ccaccatttc caactcgaat tgtcaaaagt gt					32

```
<210> SEQ ID NO 55
<211> LENGTH: 25
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (25)..(25)
<223> OTHER INFORMATION: t-benzyldA

<400> SEQUENCE: 55
ctcctgtatc tataaatgaa gagaa                                             25

<210> SEQ ID NO 56
<211> LENGTH: 25
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (25)..(25)
<223> OTHER INFORMATION: t-butylbenzyldA

<400> SEQUENCE: 56
ctcctgtatc tataaatgaa gagaa                                             25

<210> SEQ ID NO 57
<211> LENGTH: 27
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (27)..(27)
<223> OTHER INFORMATION: t-benzyldA

<400> SEQUENCE: 57
gatttctgat aatggctgtg gaataaa                                           27

<210> SEQ ID NO 58
<211> LENGTH: 27
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (27)..(27)
<223> OTHER INFORMATION: t-butylbenzyldA

<400> SEQUENCE: 58
gatttctgat aatggctgtg gaataaa                                           27

<210> SEQ ID NO 59
<211> LENGTH: 27
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (27)..(27)
<223> OTHER INFORMATION: t-benzyldA

<400> SEQUENCE: 59
gaattatctc ctgtatctat aaatgaa                                           27
```

<210> SEQ ID NO 60
<211> LENGTH: 27
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (27)..(27)
<223> OTHER INFORMATION: t-butylbenzyldA

<400> SEQUENCE: 60
gaattatctc ctgtatctat aaatgaa                                27

<210> SEQ ID NO 61
<211> LENGTH: 24
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (24)..(24)
<223> OTHER INFORMATION: t-benzyldC

<400> SEQUENCE: 61
agtaacagca agttcacttt tgtc                                   24

<210> SEQ ID NO 62
<211> LENGTH: 24
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (24)..(24)
<223> OTHER INFORMATION: t-butylbenzyldC

<400> SEQUENCE: 62
agtaacagca agttcacttt tgtc                                   24

<210> SEQ ID NO 63
<211> LENGTH: 23
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (23)..(23)
<223> OTHER INFORMATION: t-benzyldA

<400> SEQUENCE: 63
caggtgatat cgcgaagaac aca                                    23

<210> SEQ ID NO 64
<211> LENGTH: 23
<212> TYPE: DNA
<213> ORGANISM: Artificial Sequence
<220> FEATURE:
<223> OTHER INFORMATION: Mlh 1a forward primer
<220> FEATURE:
<221> NAME/KEY: modified_base
<222> LOCATION: (23)..(23)
<223> OTHER INFORMATION: t-butylbenzyldA

<400> SEQUENCE: 64
caggtgatat cgcgaagaac aca                                    23

<210> SEQ ID NO 65
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-benzyldA

<400> SEQUENCE: 65
ggaatatttg attttggaat ttcaga                                          26

<210> SEQ ID NO 66
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-butylbenzyldA

<400> SEQUENCE: 66
ggaatatttg attttggaat ttcaga                                          26

<210> SEQ ID NO 67
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-benzyldA

<400> SEQUENCE: 67
ccaaatgaac tttcttctgt tttaga                                          26

<210> SEQ ID NO 68
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-butylbenzyldA

<400> SEQUENCE: 68
ccaaatgaac tttcttctgt tttaga                                          26

<210> SEQ ID NO 69
<211> LENGTH: 27
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (27)..(27)
<223> OTHER INFORMATION: t-benzyldC

<400> SEQUENCE: 69 atttgattt  ggaatttcag  agttttc                                              27

<210> SEQ ID NO 70
<211> LENGTH: 27
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (27)..(27)
<223> OTHER INFORMATION: t-butylbenzyldC

<400> SEQUENCE: 70 atttgattt  ggaatttcag  agttttc                                              27

<210> SEQ ID NO 71
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-benzyldC

<400> SEQUENCE: 71
ctgaagactt  ggaatagatg  tactgc                                              26

<210> SEQ ID NO 72
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-butylbenzyldC

<400> SEQUENCE: 72
ctgaagactt  ggaatagatg  tactgc                                              26

<210> SEQ ID NO 73
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-benzyldA

<400> SEQUENCE: 73 ggcatccta  ataaaacaaa  agcaaa                                               26

<210> SEQ ID NO 74
<211> LENGTH: 26
<212> TYPE: DNA
<213> ORGANISM: Artificial Sequence
<220> FEATURE:
<223> OTHER INFORMATION: Mlh 1a reverse primer
<220> FEATURE:
<221> NAME/KEY: modified_base
<222> LOCATION: (26)..(26)
<223> OTHER INFORMATION: t-butylbenzyldA

<400> SEQUENCE: 74

-continued ggcatcctta ataaaacaaa agcaaa                                          26

<210> SEQ ID NO 75
<211> LENGTH: 32
<212> TYPE: DNA
<213> ORGANISM: Artificial Sequence
<220> FEATURE:
<223> OTHER INFORMATION: Mlh 1a probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 75
aaaatccaag aaaaagagca agaagaaatc ct                                   32

<210> SEQ ID NO 76
<211> LENGTH: 32
<212> TYPE: DNA
<213> ORGANISM: Artificial Sequence
<220> FEATURE:
<223> OTHER INFORMATION: Mlh 1a probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 76
cacctctgaa tccaaatgta gttacgttcc tt                                   32

<210> SEQ ID NO 77
<211> LENGTH: 32
<212> TYPE: DNA
<213> ORGANISM: Artificial Sequence
<220> FEATURE:
<223> OTHER INFORMATION: Mlh 1a probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 77
cttgctcttt ttcttggatt ttctgtatct ga                                   32

<210> SEQ ID NO 78
<211> LENGTH: 32
<212> TYPE: DNA
<213> ORGANISM: Artificial Sequence
<220> FEATURE:
<223> OTHER INFORMATION: Mlh 1a probe
<220> FEATURE:
<221> NAME/KEY: misc_feature
<223> OTHER INFORMATION: 5' FAM

```
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 78
ttcaaaccaa tcaaaccaac aaaagaatga gc                                    32

<210> SEQ ID NO 79
<211> LENGTH: 32
<212> TYPE: DNA
<213> ORGANISM: Artificial Sequence
<220> FEATURE:
<223> OTHER INFORMATION: Mlh 1a probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 79
aaaaccgctg attctttgag ttgtttttg gc                                     32

<210> SEQ ID NO 80
<211> LENGTH: 25
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (25)..(25)
<223> OTHER INFORMATION: t-benzyldA

<400> SEQUENCE: 80
gcaatctggg atctcaacaa ggaaa                                            25

<210> SEQ ID NO 81
<211> LENGTH: 25
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (25)..(25)
<223> OTHER INFORMATION: t-butylbenzyldA

<400> SEQUENCE: 81
gcaatctggg atctcaacaa ggaaa                                            25

<210> SEQ ID NO 82
<211> LENGTH: 21
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (21)..(21)
<223> OTHER INFORMATION: t-benzyldC

<400> SEQUENCE: 82
```

```
tttcatcgga cagggcaatc c                                              21

<210> SEQ ID NO 83
<211> LENGTH: 21
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (21)..(21)
<223> OTHER INFORMATION: t-butylbenzyldC

<400> SEQUENCE: 83
tttcatcgga cagggcaatc c                                              21

<210> SEQ ID NO 84
<211> LENGTH: 26
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (26)..(26)
<223> OTHER INFORMATION: t-benzyldA

<400> SEQUENCE: 84
gagggaccac aagaagaagt cgttca                                         26

<210> SEQ ID NO 85
<211> LENGTH: 26
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (26)..(26)
<223> OTHER INFORMATION: t-butylbenzyldA

<400> SEQUENCE: 85
gagggaccac aagaagaagt cgttca                                         26

<210> SEQ ID NO 86
<211> LENGTH: 24
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (24)..(24)
<223> OTHER INFORMATION: t-benzyldC

<400> SEQUENCE: 86
gacgagggac cacaagaaga agtc                                           24

<210> SEQ ID NO 87
<211> LENGTH: 24
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (24)..(24)
<223> OTHER INFORMATION: t-butylbenzyldC
```

<400> SEQUENCE: 87
gacgagggac cacaagaaga agtc                                          24

<210> SEQ ID NO 88
<211> LENGTH: 21
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (21)..(21)
<223> OTHER INFORMATION: t-benzyldC

<400> SEQUENCE: 88
cagagatcat ccagccagat c                                             21

<210> SEQ ID NO 89
<211> LENGTH: 21
<212> TYPE: DNA
<213> ORGANISM: Artificial Sequence
<220> FEATURE:
<223> OTHER INFORMATION: CRN forward primer
<220> FEATURE:
<221> NAME/KEY: modified_base
<222> LOCATION: (21)..(21)
<223> OTHER INFORMATION: t-butylbenzyldC

<400> SEQUENCE: 89
cagagatcat ccagccagat c                                             21

<210> SEQ ID NO 90
<211> LENGTH: 24
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (24)..(24)
<223> OTHER INFORMATION: t-benzyldA

<400> SEQUENCE: 90
ggttgtaatc tggaaggtcg agaa                                          24

<210> SEQ ID NO 91
<211> LENGTH: 24
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (24)..(24)
<223> OTHER INFORMATION: t-butylbenzyldA

<400> SEQUENCE: 91
ggttgtaatc tggaaggtcg agaa                                          24

<210> SEQ ID NO 92
<211> LENGTH: 23
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (23)..(23)
<223> OTHER INFORMATION: t-benzyldC

```
<400> SEQUENCE: 92
aacgtcagga acatcccaaa ggc                                              23

<210> SEQ ID NO 93
<211> LENGTH: 23
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (23)..(23)
<223> OTHER INFORMATION: t-butylbenzyldC

<400> SEQUENCE: 93
aacgtcagga acatcccaaa ggc                                              23

<210> SEQ ID NO 94
<211> LENGTH: 27
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (27)..(27)
<223> OTHER INFORMATION: t-benzyldA

<400> SEQUENCE: 94
gcgagttggc ttatcaaggt tcatgaa                                          27

<210> SEQ ID NO 95
<211> LENGTH: 27
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (27)..(27)
<223> OTHER INFORMATION: t-butylbenzyldA

<400> SEQUENCE: 95
gcgagttggc ttatcaaggt tcatgaa                                          27

<210> SEQ ID NO 96
<211> LENGTH: 22
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (22)..(22)
<223> OTHER INFORMATION: t-benzyldC

<400> SEQUENCE: 96
gttgattgga tagcgagttg gc                                               22

<210> SEQ ID NO 97
<211> LENGTH: 22
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (22)..(22)
```

<223> OTHER INFORMATION: t-butylbenzyldC

<400> SEQUENCE: 97
gttgattgga tagcgagttg gc                                        22

<210> SEQ ID NO 98
<211> LENGTH: 21
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (21)..(21)
<223> OTHER INFORMATION: t-benzyldC

<400> SEQUENCE: 98
ctcgtcgaca acttcctcct c                                         21

<210> SEQ ID NO 99
<211> LENGTH: 21
<212> TYPE: DNA
<213> ORGANISM: Artificial Sequence
<220> FEATURE:
<223> OTHER INFORMATION: CRN reverse primer
<220> FEATURE:
<221> NAME/KEY: modified_base
<222> LOCATION: (21)..(21)
<223> OTHER INFORMATION: t-butylbenzyldC

<400> SEQUENCE: 99
ctcgtcgaca acttcctcct c                                         21

<210> SEQ ID NO 100
<211> LENGTH: 32
<212> TYPE: DNA
<213> ORGANISM: Artificial Sequence
<220> FEATURE:
<223> OTHER INFORMATION: CRN probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 100
ccaagactca acattcaact cattatctaa cg                             32

<210> SEQ ID NO 101
<211> LENGTH: 31
<212> TYPE: DNA
<213> ORGANISM: Artificial Sequence
<220> FEATURE:
<223> OTHER INFORMATION: CRN probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 101
acatcacata ctcaccacat aatccaaatc t    31

<210> SEQ ID NO 102
<211> LENGTH: 31
<212> TYPE: DNA
<213> ORGANISM: Artificial Sequence
<220> FEATURE:
<223> OTHER INFORMATION: CRN probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 102
acaatgccaa ctggaagata agtaaagtag t    31

<210> SEQ ID NO 103
<211> LENGTH: 32
<212> TYPE: DNA
<213> ORGANISM: Artificial Sequence
<220> FEATURE:
<223> OTHER INFORMATION: CRN probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 103
acaatgccaa ctggaagata agtaaagtag tt    32

<210> SEQ ID NO 104
<211> LENGTH: 32
<212> TYPE: DNA
<213> ORGANISM: Artificial Sequence
<220> FEATURE:
<223> OTHER INFORMATION: CRN probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 104
ttggaagatg ggatttgtca actgtcaatc tg    32

<210> SEQ ID NO 105
<211> LENGTH: 31
<212> TYPE: DNA
<213> ORGANISM: Artificial Sequence
<220> FEATURE:
<223> OTHER INFORMATION: CRN probe
<220> FEATURE:
<221> NAME/KEY: misc_feature
<223> OTHER INFORMATION: 5' FAM

```
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 105
ttggaagatg ggatttgtca actgtcaatc t                                        31
```